US005873823A

United States Patent [19]
Eidelberg et al.

[11] Patent Number: 5,873,823
[45] Date of Patent: Feb. 23, 1999

[54] MARKERS FOR USE IN SCREENING PATIENTS FOR NERVOUS SYSTEM DYSFUNCTION AND A METHOD AND APPARATUS FOR USING SAME

[76] Inventors: David Eidelberg, 250 E. 87th St., Apt. 17-E, New York, N.Y. 10128; James R. Moeller, 201 Varsity Ave., Princeton, N.J. 08540

[21] Appl. No.: 706,478

[22] Filed: Sep. 4, 1996

Related U.S. Application Data

[63] Continuation of Ser. No. 379,056, Jan. 27, 1995, Pat. No. 5,632,276.
[51] Int. Cl.$^6$ ............................................. A61B 5/05
[52] U.S. Cl. .................................................. 600/407
[58] Field of Search ................................ 128/653.1, 920, 128/923; 364/413.13, 413.02, 413.15; 324/245, 248; 600/407, 544

[56] References Cited

U.S. PATENT DOCUMENTS

| | | | |
|---|---|---|---|
| 4,188,956 | 2/1980 | John | 600/544 |
| 4,307,726 | 12/1981 | Paulson et al. | 128/653.1 |
| 4,736,751 | 4/1988 | Gevins et al. | 600/545 |
| 4,977,896 | 12/1990 | Robinson et al. | 600/409 |
| 5,083,571 | 1/1992 | Prichep | 600/544 |
| 5,215,095 | 6/1993 | Macvicar et al. | 128/665 |
| 5,262,945 | 11/1993 | DeCarli et al. | 364/413.13 |
| 5,269,325 | 12/1993 | Robinson et al. | 600/409 |
| 5,299,119 | 3/1994 | Kraf et al. | 364/413.02 |
| 5,302,583 | 4/1994 | Costa et al. | 514/30 |
| 5,331,969 | 7/1994 | Silberstein | 600/544 |
| 5,438,989 | 8/1995 | Hochman et al. | 128/653.1 |
| 5,445,937 | 8/1995 | Haley | 435/6 |

OTHER PUBLICATIONS

Moeller, et al., "The Metabolic Topography of Normal Healthy Aging," *Neurology*, 44 (Supplement 2), p. A164, Apr. 1994.

Moeller, et al., "The Metabolic Topography of Normal Aging," *Journal of Cerebral Blood Flow and Metabolism*,", vol. 15 (Supplement 1), p. S593, Jul. 1995.

Moeller, et al., "The Metabolic Topography of Normal Aging,"*Journal of Cerebral Blood Flow and Metabolism*,", 16 (No. 3), pp. 385–398, 1996.

Alexander, G.E. and J.R. Moeller, "Application of Scaled Subprofile Model Analysis to Functional Imaging of Neurological Disorders: A Principal Component Approach to Modeling Regional Patterns of Brain Function in Disease," *"Human Brain Mapping*, 2, pp. 79–94, 1994.

Eidelberg, et al., "Variability in Regional Cerebral Metabolic Rate for Glucose (rCMRGlu) and its Consequences for the Study of Neurological Disease with FDG/PET,"*Neurology*, 38 (Supplement 1), p. 367, Mar. 1988.

Eidelberg, et al., "The Metabolic Anatomy of Parkinson's Disease: complementary [18f] fluorodeoxyglucose and [18f] fluorodopa positron emission tomographic studies," *Movement disorders*, 5(3), pp. 203–213, 1990.

(List continued on next page.)

*Primary Examiner*—Brian Casler
*Attorney, Agent, or Firm*—Akin, Gump, Strauss, Hauer & Feld, L.L.P.

[57] ABSTRACT

A marker for use in screening patients for nervous system dysfunction and a method of producing the marker. The marker is a digital profile of a brain having a particular nervous system dysfunction that is used for screening patients for that nervous system dysfunction. The digital profile consists of a grid of values that are a numerical representation of graphical images of functional activity in the brain having that nervous systems dysfunction. The marker is produced by selecting a nervous system dysfunction and by creating a digital profile of predetermined functional activity at a plurality of sets of predetermined coordinates of a given brain geometry. The marker can also be used to screen patients for any specific functional brain activity not limited to nervous system dysfunctions.

21 Claims, 4 Drawing Sheets

OTHER PUBLICATIONS

Eidelberg, et al., "The Metabolic Pathology of Parkinson's Disease: Complementary 18F–Fluorodopa and 18F–Fluorodeoxyglucose PET Studies," 39(3), (Supplement 1), p. 273, Mar. 1989.

Eidelberg, et al., "The Metabolic Topography of Parkinsonism," *J. Cereb. Blood Flow Metab.*, 14(5), Supplement 1, pp. 783–801, Sep. 1994.

Eidelberg, et al., "Brain Metabolic Topography In Parkinsonism," vol. 43(4), Supp. 2, Apr. 1993, p. A270.

Eidelberg, et al., "Brain Metabolic Topography in the Movement Disorders," *Journal of Cerebral Blood Flow and Metabolism*, vol. 13, (Supplement 1), p. S9, 1993.

Eidelberg, et al., "The Metabolic Topography of Idiopathic Torsion Dystonia," *Brain*, 118 (Pt. 6), pp. 1473–1484, 1995.

Eidelberg, et al., "Brain Metabolic Topography in Idiopathic Torsion Dystonia," vol. 43(4), (Supplement 2), P. A408, Apr. 1993.

Eidelberg, et al., "Early Differential Diagnosis of Parkinson's Disease with 18F–flourodeoxyglucose and positron emission tomography," *Neurology*, 45(11), pp. 1995–2004, Nov. 1995.

Eidelberg, et al., "Detection of Early Parkinson's Disease with 18–F Fluorodeoxyglucose and Positron Emission Tomography," *Neurology*, 44 (Supplement 2), p. A352, Apr. 1994.

Eidelberg, et al., "Detection of Early Parkinson's Disease with 18–F Fluorodeoxyglucose and Positron Emission Tomography," *Journal of Nuclear Medicine*, No. 31, 10P, 1994.

Eidelberg, et al., "Assessment of Disease Severity in Parkinsonism with fluorine–18–fluorodeoxyglucose and PET," *Journal of Nuclear Medicine*, 36(3), pp. 378–383, Mar. 1995.

Ishikawa, et al., "FDG/PET Predicts Clinical Disability in Parkinson's Disease," *Neurology*, 44.4 (Supplement 2), p. A280, May 1994.

Spetsieris, et al., "Visualizing the Evolution of Abnormal Metabolic Networks in the brain using PET," *Comput. Med. Imaging Graph*, 19(3), pp. 295–306, 1995.

Spetsieris, et al., "Visualizing Patterns of Neurological Disease Progression with PET," *Physics of Medical Imaging*, pp. 2168–2227, Feb. 1994.

MARKERS FOR USE IN SCREENING PATIENTS FOR NERVOUS SYSTEM DYSFUNCTION AND A METHOD AND APPARATUS FOR USING SAME

This application is a continuation of application Ser. No. 08/379,056, filed Jan. 27, 1995 now U.S. Pat. No. 5,632,276.

BACKGROUND OF THE INVENTION

The present invention is directed to the screening of patients for nervous system dysfunction including neurological or psychiatric degenerative conditions.

Functional brain imaging by means of positron emission tomography (PET) and single photon emission computed tomograph (SPECT) is known, but up to now, has been applied mainly for research purposes and has had limited diagnostic applicability.

Currently, a neurological diagnosis utilizing a functional brain image requires the interaction of a trained physician or technologist to first manually identify brain regions on the image using an anatomical chart and then to visually compare changes in single brain regions independently of other regions.

SUMMARY OF THE INVENTION

The main object of the present invention is to provide a marker for use in screening patients for nervous system dysfunction.

This object is achieved in accordance with the invention by the use of a marker having a profile of predetermined functional activity at a plurality of sets of predetermined coordinates of a given brain geometry. Each set of the predetermined coordinates preferably has a single numerical value associated therewith corresponding to functional activity. Preferably, each set of coordinates corresponds to a region of interest in a patient's brain with each region of interest preferably having a volume of no greater than about 1 $cm^3$. In a particularly advantageous embodiment of the present invention, each region of interest comprises at least one pixel of at least one slice of a corresponding brain scan and the profile comprises an array of values for each slice of the corresponding brain scan.

Each pixel has a value associated with it which is the relative contribution of brain activity in the volume defined by the pixel.

In accordance with the invention, the markers are used for the diagnosis of Parkinson's disease, Alzheimer's disease, torsion dystonia, cerebellar degeneration, depression, premature aging and neurological AIDS.

Another object of the present invention is to provide a method for screening patients for nervous system dysfunction.

This object is achieved in accordance with the present invention by a method comprising producing a patient profile of actual functional activity of a brain of a patient and comparing the patient profile with at least one marker comprising a profile of predetermined functional activity at a plurality of sets of predetermined coordinates of a given brain geometry.

The method preferably comprises comparing the patient profile with a plurality of markers for different nervous system dysfunctions. In this way, the same scan can be used for screening for different nervous system dysfunctions and the inconvenience of putting a patient through multiple brain scans is eliminated.

The plurality of markers can be for nervous system dysfunction selected from Parkinson's disease, Alzheimer's disease, torsion dystonia, cerebellar degeneration, depression, premature aging and neurological AIDS.

The patient profile is produced according to the present invention preferably by calculating numerical values of functional activities of a plurality of regions of interest of the brain of the patient corresponding to the plurality of sets of predetermined coordinates of the given brain geometry. The step of calculating preferably comprises producing a single numerical value for each region of interest.

A further object of the present invention is to provide an apparatus for determining the presence or severity of nervous system dysfunction in a patient.

This object is achieved in accordance with the present invention by providing an apparatus including a memory storing at least one marker for a nervous system dysfunction comprising a profile of predetermined functional activity at a plurality of sets of predetermined coordinates of a given brain geometry. A pre-processor is receptive of data corresponding to functional activity of a brain of a patient for producing a patient profile of functional activity for each of a plurality of regions of interest of the patient's brain corresponding to the plurality of sets of predetermined coordinates of the given brain geometry. A processor cross-correlates the patient profile with the at least one marker and a post-processor determines the presence or severity of a nervous system dysfunction as a function of the degree of covariance for the cross-correlation.

In accordance with the present invention, the apparatus preferably comprises a scanner for scanning the patient's brain to produce the data applied to the pre-processor. The scanner preferably comprises one of a PET scanner, a SPECT scanner and a functional MRI scanner.

The pre-processor preferably comprises a spatial filter for filtering the data and circuitry for performing a log transform on the filtered data.

The post-processor preferably comprises circuitry for rescaling the degree of covariance to produce a patient marker score and circuitry for comparing a patient marker score with a previously obtained patient marker score for the patient to determine severity of a dysfunction.

Further in accordance with the present invention, a plurality of markers are preferably stored in memory and the processor cross-correlates the patient profile with the plurality of markers. The plurality of markers preferably are for nervous system dysfunctions including Alzheimer's disease, torsion dystonia, cerebellar degeneration, Parkinson's disease, neurological AIDS, depression and premature aging.

Further in accordance with the present invention, the scanner can be disposed at a remote location from the pre-processor and thus the apparatus further comprises data communication circuitry for transmitting data from the scanner to the pre-processor. The communication can be made by means of wire or wireless transmission, can be carried out by modem over telephone lines or by other networking techniques.

Another object of the present invention is to provide a method for determining the presence or severity of a nervous system dysfunction in a patient.

This object is achieved in accordance with the present invention by a method comprising providing at least one marker for a nervous system dysfunction comprising a profile of predetermined functional activity at a plurality of sets of predetermined coordinates of a given brain geometry, producing a patient profile or functional activity for each of a plurality of regions of interest of a patient's brain corresponding to the plurality of sets of predetermined coordinates of the given brain geometry, cross-correlating the patient profile with the at least one marker and determining the presence or severity of a nervous system dysfunction as a function of the degree of covariance for the cross-correlation.

In accordance with the present invention, the method further comprises scanning the patient's brain to produce data for the patient profile. The scanning preferably comprises one of PET scanning, SPECT scanning and functional MRI scanning.

The step of producing the patient profile preferably comprises spatially filtering the data and performing a log transform on the filtered data.

The step of determining the presence or severity of the dysfunction preferably comprises resealing the degree of covariance to produce a patient's score for the marker. Preferably, the method compares the patient's score for the marker with the patient's previous score for that marker to determine the progressive changes in the dysfunction over time.

In a preferred embodiment of the present invention, a plurality of markers are provided and the step of cross-correlating comprises cross-correlating with the plurality of markers so that a single scan can be used for various dysfunctions such as Alzheimer's disease, torsion dystonia, cerebellar degeneration, Parkinson's disease, neurological AIDS, depression and premature aging.

The method can preferably be carried out with the scanning performed remotely from the processing of the data from the scan by transmitting data from the scanner to the location where the processing is carried out.

In a further preferred embodiment of the present invention, the step of determining the presence or severity of the given nervous system dysfunction is achieved by comparing the patient's score with a distribution of patients' scores of a patient population having the given nervous system dysfunction, a distribution of patients' scores of a patient population having a different nervous system dysfunction and a distribution of patients' scores of a patient population not having the given nervous system dysfunction.

The present invention embodies the realization that a pattern of regional brain metabolic activity could be used clinically as part of a marker for the presence or absence of neurodegenerative conditions including Parkinson's disease, Alzheimer's disease, torsion dystonia, cerebellar degeneration and neurological AIDS as well as a gauge for assessing disease severity in these and related conditions. This method may also be used as a screen to determine whether a subject's brain function is age-appropriate, that is, whether or not there is premature neurological aging.

The clinical use of the marker comprises receiving functional brain data from an individual subject's PET, SPECT or functional MRI scans and calculating the degree of expression of the marker in an individual.

Another embodiment of the present invention is the use of a marker diagnostically on a case-by-case basis and developing a computational basis for diagnosing and objectively rating disease severity and progression in a strictly automated fashion. The method and apparatus of the present invention involves the automated application of a marker to individual subject scans for the purpose of diagnosis without reliance upon direct user visualization of images.

The method and apparatus in accordance with the present invention is applicable to any functional imaging modality, including PET, SPECT and functional MRI. Moreover, the method and apparatus can be used with any disease-related network in its analysis of individual scans and thus act as a marker for differential diagnosis.

For example, in the work-up of an elderly patient who is felt to be cognitively impaired, the physician can pose a variety of possibilities including normal aging, Alzheimer's disease, Parkinson's disease, depression, etc. The invention will produce a statistical likelihood of occurrence for each diagnostic possibility.

The present invention can be used as a means of disease detection, as a means of assessing the severity of a particular disease and as a means of age-appropriateness of brain function as a screening technique for the assessment of cognitive functioning in the elderly.

The present invention achieves the determination of the presence or severity of the disease by cross-correlating a brain tomographic image obtained by PET, SPECT or functional MRI as an array of pixels, with a multi-regional topographic marker whose expression indicates the presence and/or severity of a particular disease. The cross-correlation using covariance analysis produces a data set including a patient score which quantifies the degrees of expression of the disease-related marker in the individual functional image. A differential diagnosis can be constructed based on the relationship of the calculated individual patient subject score to known distributions of subject scores for the particular marker in the given disease, as well as distributions of scores in populations with related but different diseases and in normal control populations. Based upon those distributions, a likelihood ratio of having the given disease will be produced for a physician.

The marker allows for extraction diagnostic network information from functional brain images. Anatomical imaging techniques, such as magnetic resonance imaging (MRI) and computer tomography (CT), are restricted to showing gross structural changes in brain tissue, whereas functional brain imaging with positron emission tomography (PET), single photon emission computed tomography (SPECT) and functional MRI have the capacity to quantify actual regional brain function.

The markers herein allow for the identification and measurement of small abnormalities in brain networks which arise from multiple brain regions that are functionally and/or anatomically interconnected. This is based on the fact that the data from the whole brain can be analyzed as a set of networks each comprising the interrelated (covarying) metabolic activity from individual brain regions. The present invention explores the functional brain data on an individual case basis for the presence or absence of a diagnostic marker. By quantifying the extent to which any marker is represented in a given subject's brain image, the present invention allows a physician to diagnose Parkinson's disease at its earliest stages, separate drug responsive Parkinson's disease from drug-resistant look-alikes and monitor the severity of the illness over time. Similarly, diagnosis and/or severity determinations can be made for Alzheimer's disease using PET and SPECT modalities and for the assessment of the normal aging process.

The present invention is particularly useful in the diagnosis and assessment of neurodegenerative and psychiatric disorders. These conditions entail primarily Alzheimer's disease and related forms of dementia, as well as Parkinson's disease and allied movement disorders. These diseases are notoriously difficult to diagnose with accuracy, because CT scans and MRI typically appear normal in the face of significant clinical abnormalities. Functional brain images with PET or SPECT can be used with disease-related markers of the present invention to diagnose these conditions with great accuracy. In addition, the present invention is capable of providing an objective rating of disease severity to assess the efficacy of treatment and the rate of progression of an illness in treated and untreated states.

These results can have a major impact in the planning of appropriate pharmacotherapy as well as in the clinical assessment of these disorders.

In addition, the capacity to gauge the effects of normal aging on a case by case basis can afford neurologists, psychiatrists and geriatricians a valuable tool in determining whether a given individual is performing according to his or her chronological age. The invention is therefore a valuable screen with which to examine individuals suspected of having neurodegenerative disease at an early stage prior to the development of clear-cut behavioral deficits.

The present invention is an important tool for the clinical assessment of elderly patients in whom such a neurodegenerative disorder is suspected, as well as in the ongoing care of those in whom a neurodegenerative disorder has already been diagnosed. Because of the capacity of the present invention to provide differential diagnostic probability information on an automated basis, the invention has vast applicability in neurology, psychiatry, general medicine and geriatrics.

The brain data information from the PET and SPECT sources can also be transferred through communication networks to remote sites where the analysis according to the present invention can be routinely performed. An individual subject's functional brain image can be digitized and analyzed like a database at a remote information processing center, wherein it is screened with a plurality of markers for the presence or absence of a number of specific diseases in accordance with a requesting physician's clinical differential diagnosis. By measuring subject scores for each marker for a given referred brain scan, one could provide the clinician with the numeric likelihood of a correct diagnosis.

Patient evaluation through functional brain imaging can begin with an assessment as to whether the brain function is appropriate for age, followed by a search through a standardized battery of degenerative disorders to see which is the most represented in the brain and whether this conforms with the clinical history. Alternatively, the scan of a patient with an established clinical diagnosis can be cross-correlated with a disease-specific marker to gauge the progression of disease and its response to treatment. On this basis, individuals already diagnosed can be assessed for change over a period of time without therapy or during the course of a therapeutic intervention. This technology is useful for neurological and psychiatric degenerative illnesses of the brain.

In accordance with the invention, the diagnosis can be performed without manually placed regions or visual interaction. This invention allows the brain to be divided into a set of standardized pixels (stereotaxic coordinates) and analyzed in an entirely automated fashion.

These and other features and objects of the present invention that will be achieved in accordance with the present invention will become more apparent from the following detailed description of the invention taken with the attached drawings, wherein:

BRIEF DESCRIPTION OF THE DRAWINGS

FIG. 3A is a flow chart showing details of FIG. 3;

DETAILED DESCRIPTION OF THE INVENTION

Figure 1:
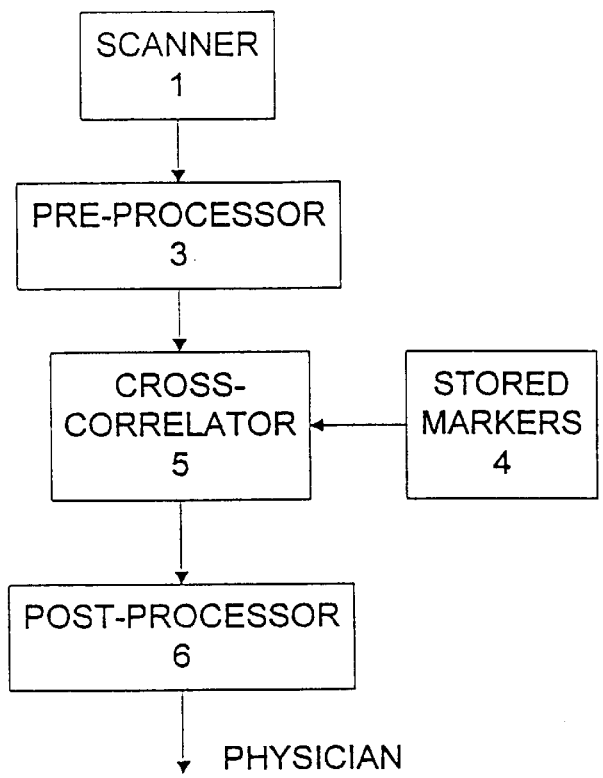
FIG. 1 is a block diagram of the apparatus for screening patients for nervous system dysfunction in accordance with the present invention.

Referring to FIG. 1, a tomographic scanner 1, such as a PET scanner, a SPECT scanner or a functional MRI scanner, produces data corresponding to the functional activity of a patient's brain. This data is in the form of an array corresponding to the geometry of the particular patient's brain.

For example, a PET scanner typically produces between 14 and 35 slices, with corresponding slice thickness of between 5 and 8 millimeters. Within each slice, the size of the array is a function of the linear resolution of the scanner. Typically a 5 millimeter linear resolution will be produced for 1,024×1,024 pixels for each slice, whereas a 1 centimeter linear resolution will be produced for 512×512 pixels per slice. In accordance with the invention, the linear resolution should be at least 256×256 producing pixels ranging from 0.1 $cm^3$ to 10 $cm^3$.

Figure 3:
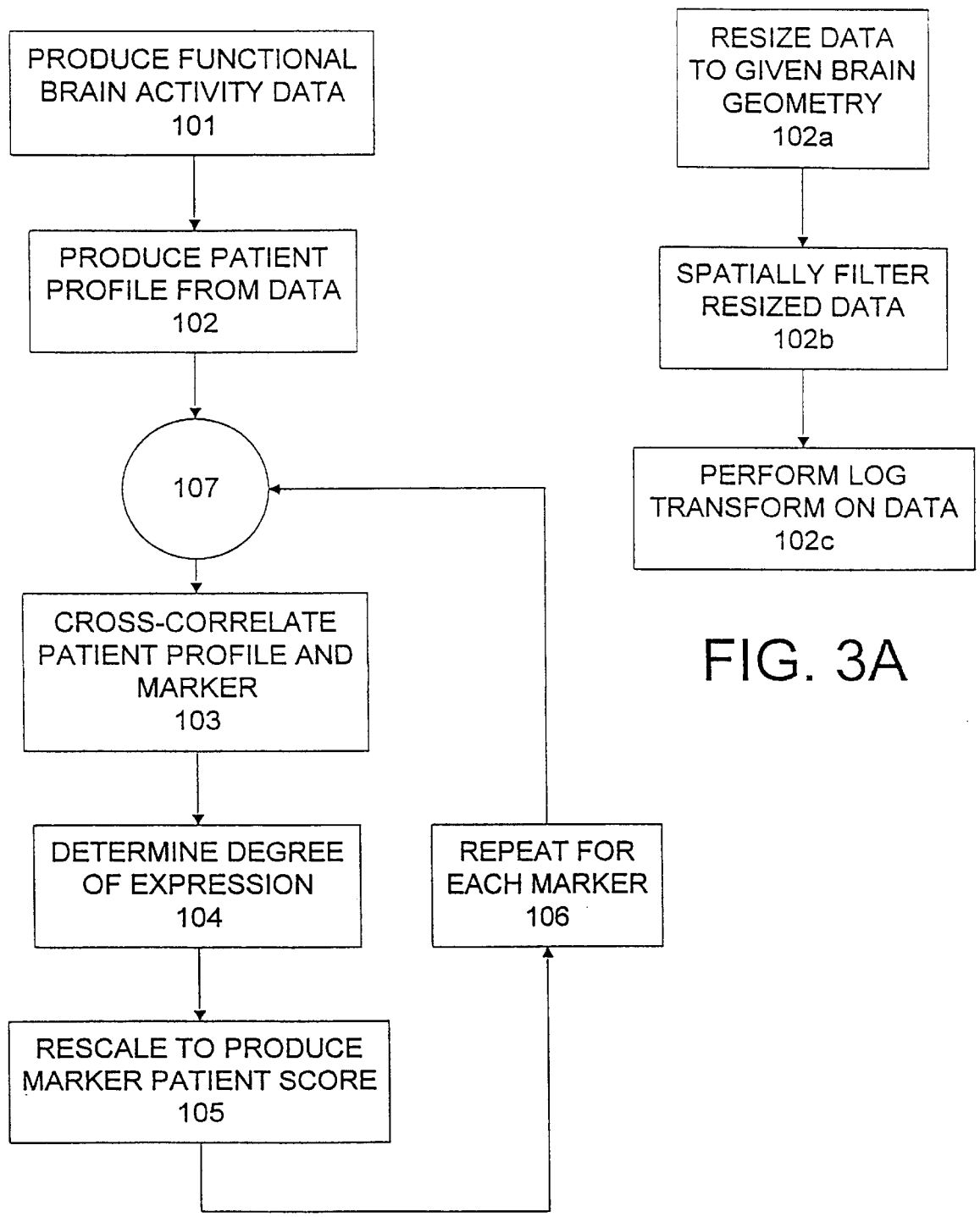
FIG. 3 is a flow chart of the method according to the present invention.

The output of the scanner in step 101 of FIG. 3 is an array of data which is applied to a pre-processor 3 which produces a patient profile from the data in step 102.

Details of the production of the patient profile carried out in pre-processor 3, are set forth in the steps of FIG. 3A. As shown therein, the data is first resized and reoriented in step 102a to correspond to a given brain geometry (stereotoxic coordinate system) that has been selected for the purpose of this invention.

The given brain geometry discussed hereinafter, has been defined using the Talairach atlas coordinates. Other standardized brain atlas coordinate systems could also be used to define a given brain geometry within the scope of the present invention.

The resized data is then spatially filtered in step 102b in a low pass spatial filter to reduce noise and to produce a more limited size array of data. This allows the individual differences in brain configuration to be minimized such that all brain slices can be placed in a common coordinate system. The spatial filter can be a Gaussian filter or another type of low pass filter. A spatial filter suitable for use herein is described in Kak and Slaney, *Principles of Computed Tomographic Imaging*, IEEE Press, New York, 1987, pp. 40, 41, 226, which is incorporated herein by reference.

Figure 5:
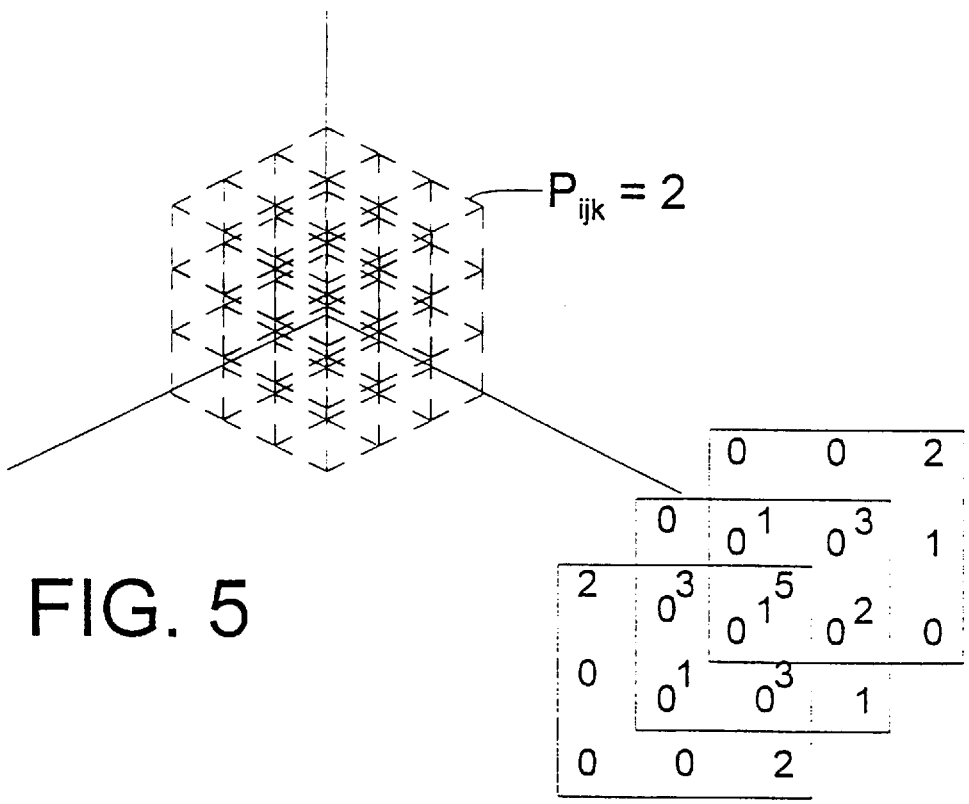
FIG. 5 illustrates a region of a brain and the numerical values associated therewith before processing.
Figure 6:
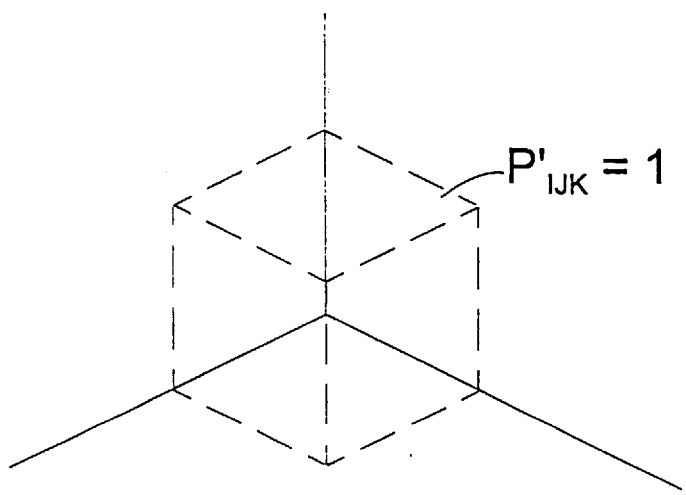
FIG. 6 shows the region after processing with the single value associated therewith.

In FIG. 5, one region of the brain is illustrated by a group of 27 pixels each having a volume on the order of 1 $cm^3$ and each having a numerical value associated therewith and corresponding to the brain activity at that pixel. The array of numbers shown in FIG. 5 correspond to the values for each of the pixels. For example, the pixel $P_{ijk}$ has a functional value equal to 2. The spatial filtering of the array effectively produces a pixel volume of 27 $cm^3$ with an average value for the overall region so that the resulting single pixel $P'_{IJK}$ has a value of 1. Thus the resulting array will have $\frac{1}{27}$ the number of pixel values.

The pre-processor 3 also performs a log transform on the data in step 102c so as to allow the subtraction of global effects (metabolic activity that affects all brain regions equally) from an individual's brain scan.

In step 103, the output of the pre-processor 3 is then cross-correlated in cross-correlator 5 with at least one stored marker stored in memory 4. The cross-correlation is carried out according to the equation $$\frac{\sum_i P_i \cdot M_i}{N}$$

where $P_i$ is the preprocessed value for each region of interest, $M_i$ is the corresponding marker value for that region of interest in which $$\sum_i M_i = 0$$

and N is the total number of regions of interest. This cross-correlation with the marker produces a single covariance value for each marker in step 104, representing the marker's expression in that data array. The post-processor 6 takes the value obtained by the cross-correlator and rescales the raw data in step 105 to produce values between 0 and 1 which are the patient or subject scores.

In accordance with step 106, steps 103–105 are repeated for each marker stored in memory 4 if a battery of tests is called for by a physician, as set forth in step 107.

Figure 4:
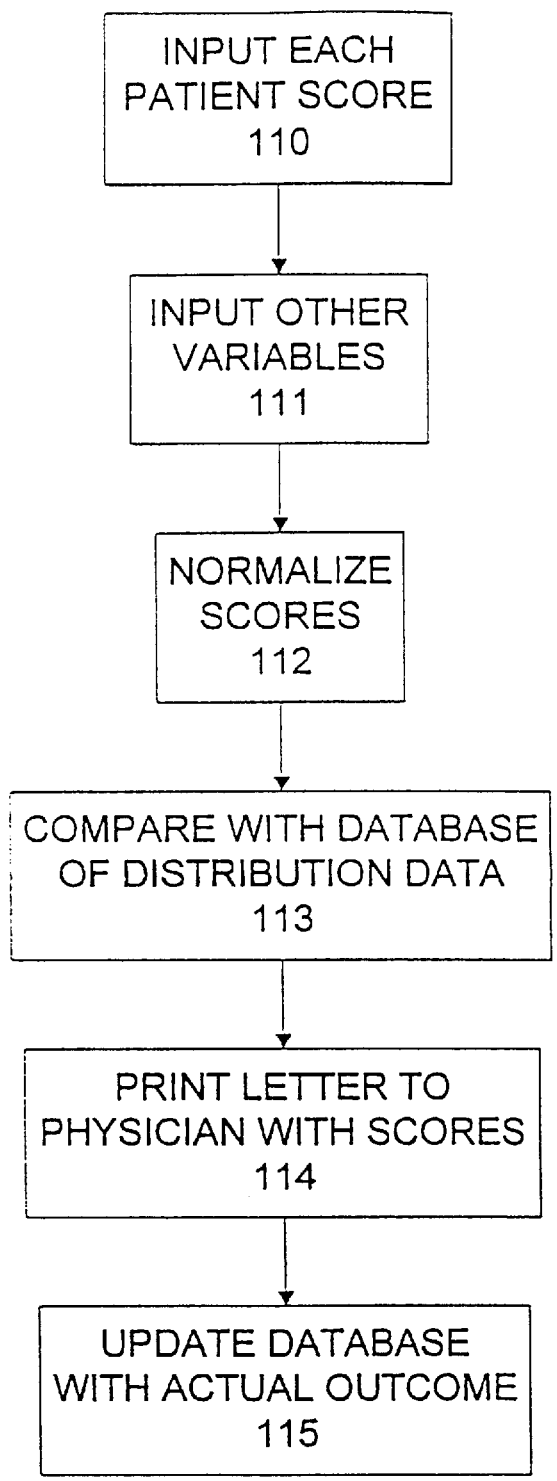
FIG. 4 is a flow chart of an additional aspect of the method of the present invention.

In accordance with the present invention, in addition to the production of patient scores, the likelihood of the patient having the dysfunction being screened for can be further determined in post-processor 6 by the steps set forth in FIG. 4.

In that procedure, the patient scores are input in step 110 and in step 111, other input variables are entered including for example, the patient's race, gender, age, weight, and clinical and medication history. These additional inputs allow the post-processor to normalize the patient scores so that they can be compared to scores of other patients with comparable demographics. The normalized data is then compared in step 113 with data distributions for the marker in an established population known to have the dysfunction in question, patient populations having different but closely related conditions, and normal control populations. This database is stored in memory 4.

Based upon the comparisons with all of the distributions, the likelihood of a patient having the dysfunction is determined, and a letter can be printed for the doctor (step 114), which includes all of the demographic data and the determined probability of dysfunction. Another important feature of the present invention is the ability to update the database with the actual outcome of the patient in step 115 so as to make the distributions more accurate for future comparisons.

The pre-processor 3, cross-correlator 5 and post-processor 6, as described hereinabove, can be implemented by a microprocessor such as an Intel 80X86, Pentium, Power PC 6100 microprocessor and more preferably in a microcomputer workstation such as those made by Hewlett-Packard or Sun Microsystems.

Figure 2:
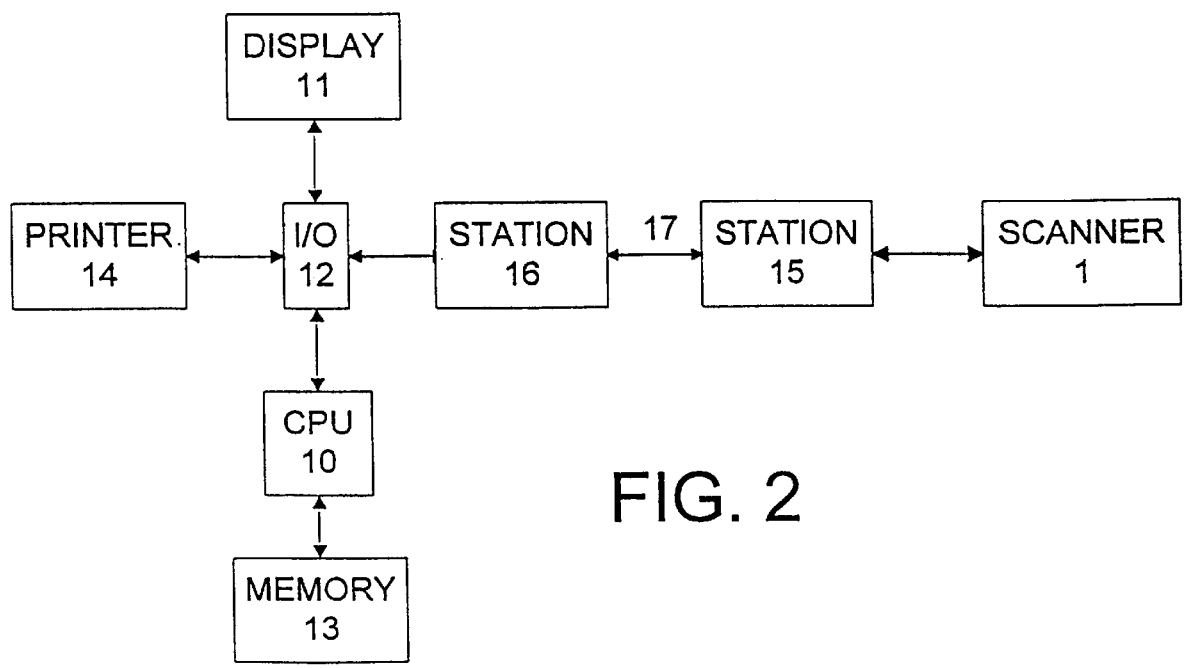
FIG. 2 is another embodiment of the apparatus of FIG. 1.

For example, the system of FIG. 2 can be used in accordance with the method to carry out the method as described. The functions of the pre-processor, post-processor and cross-correlator of FIG. 1 are carried out by a CPU 10 of a microcomputer which also has I/O 12, a memory 13 for the stored markers and databases of patient scores, a printer 14 for letters and a display for prompting the user.

In this embodiment, the scanner 1 can be remotely situated in a different city, state or country, and the functional brain data therefrom can be transmitted from station 15 having a modem or the like via a wire or wireless communications network 17 to a station 16 having a modem or the like located at CPU 10 and interfacing with I/O 12.

EXAMPLE 1

In the screening for Parkinson's disease, a patient is injected with a radiolabeled analogue of glucose (18 F-fluorodeoxyglucose) for PET imaging on scanner 1 which is a commercially available General Electric Advance Tomograph. The PET image consists of 35 parallel slices of 4.2 millimeters with 256×256 pixels per slice. The resulting data describes the regional metabolic activity of the brain in terms of glucose uptake. This data is input into pre-processor 3. The pre-processor 3, which is preferably constituted by CPU 10 and memory 13, stores the data in memory 13.

Table I depicts a portion of the data from one slice of the scan that includes the thalamic region of the patient's brain.

Because of the difference in the size and shapes of different subjects' brains, each image slice is resized and reoriented in pre-processor 3 so that it conforms to a given brain geometry with individual pixels defined in terms of a standardized three-dimensional coordinate system, preferably the Talairach Atlas coordinates.

The resized array for the data of Table I is shown in Table II with the data values omitted for the sake of clarity. This data of Table II is also stored in memory 13.

The next step in the process is spatial filtering of the data in pre-processor 3. The results of the spatial filtering for the data of Table II is shown in Table III. The spatial filtering would, of course, be carried out for all of the data in the slice and for all of the slices. The individual pixels of Table III describe metabolic activity over a larger spatial expanse than in Table I. The data is spatially filtered to minimize the effects of subject differences in brain geometry. The pixel values in Table III are less affected by local misalignments between the raw brain image and the given brain geometry than the pixel values of Table I. In Table III, the data is a single value which represents the mean of the data in groups of 12 pixels in Table II. The data of Table III is stored in memory 13.

In the next step, the values of Table III are log transformed by pre-processor 3 into natural logarithmic values shown in Table IV. The log transformation would, of course, be carried out for all of the spatially filtered data in the slice and for all of the slices. The data of Table IV is stored in memory 13.

The specific marker for Parkinson's disease stored in memory 4 is defined in terms of the same Talairach Atlas coordinate system. In order to simplify the processing, the marker is defined in terms of a series of standardized elliptical areas encompassing pixels in the resized and spatially filtered array, as illustrated in Table V. The profile for Parkinson's Disease is shown in Table VI, wherein:

| | |
|---|---|
| Z | is the horizontal plane distance of the slice from the Ac—Pc line which connects the anterior and posterior commissures, and is the standard reference line for stereotaxic coordinate systems. |
| X, Ye | are elliptical origin coordinates |
| R1, R2 | are principal axes radii |
| Ang | the acute angle that either R1 or R2 makes with the Y-axis, which is measured in the counterclockwise direction |
| LH | Left hemishpere |
| RH | Right hemisphere |

The value assigned to each volume of interest of the marker $P_{VOI}$ is the relative contribution of metabolic activity in that volume to the overall disease related covariance pattern. That is, in determining a patient's assignment to a single diagnostic category using a given marker, the relationships of covarying metabolic activity between volumes with high absolute values in the marker are, relatively speaking, of greatest diagnostic value. As shown in Table VII, all pixels within the elliptical area are assigned a value of 2.11 in the profile, and all other pixels have a value of −0.01. Because each imaging modality measures a specific aspect of local brain function, the regional weights that comprise the marker for any given nervous system dysfunction or for normal aging, can be somewhat different for PET, SPECT and functional MRI. The data of Table VII is stored in memory 13. As will be understood, each of the correlation calculations is performed in cross-correlator 5 for each of the 100 regions addressed in the marker.

In terms of individual slices, both a patient's functional image and the marker are mathematically represented as two-dimensional numeric arrays of corresponding volume values. Together the sets of slices define a three-dimensional array in which the third dimension specifies the slice position relative to a parallel reference line (e.g., Ac-Pc line) or plane. By rendering the patient's brain into an entirely digital form, the invention allows for the application of the marker to any new brain image, and permits a completely automated method of patient score calculation.

The result of the pixel-by-pixel multiplication of the two arrays of Tables IV and VII is shown in Table VIII, which is stored in memory 13. This correlation would, of course, be carried out for all of the data in the slice and for all of the slices by using the relevant marker values in Table VI. From this data which is input to post-processor 6, the covariance between the marker and the patient's profile is obtained, and this represents the strength with which the marker pattern is expressed in the functional image.

The pixel-by-pixel multiplication of the Tables IV and VII results in a value of $$\sum_i P_i \cdot M_i$$

of 35.215 for the pixels given in the region illustrated in Table V. When tables corresponding to other portions of the slice and the other slices are combined and they result in a total covariance of 0.114. The covariance statistic is a measure of the degree to which an individual expresses the given marker in his/her functional images relative to a standardized array. In this analysis, the degree to which each individual patient expressed the marker was referenced to a baseline determined by a mean array acquired across a large sample of normal subjects.

Upon rescaling in post-processor 6, the score for the patient is 0.77. The score is compared in post-processor 6 to known statistical distributions of the scores in established populations of normals and patients with the disease in question to determine the likelihood of the disease. As a result, the patient is calculated to have a likelihood of 85% that the patient is in an early stage of Parkinson's disease.

EXAMPLE 2

The patient of Example 1 is now screened for Alzheimer's Disease by utilizing the same data which is then resized, spatially filtered and log transformed to result in an array of data similar to that shown in Table IV. In this case the spatial filtering reduces the scan data in each slice to an array of 64×64 values. As a result, the doctor can perform a single scan for a patient's brain and use that same scan to screen for different nervous system dysfunctions. This reduces the inconvenience to the patient.

The specific marker is defined as a table of $64^2$ values for each slice corresponding to each pixel in the data array for each of the 35 slices.

The value assigned to each pixel $P_{VOI}$ is multiplied by the values in the spatially filtered array from the scan. Thus a calculation is performed for each of the $64^2 \times 35$ pixels.

The combined covariance yielded a value of 0.24 which, upon rescaling, produces a score for the patient of 0.15. As a result, the patient shows a likelihood of 5% that the patient is in an early stage of Alzheimer's Disease.

EXAMPLE 3

A patient is screened to determine whether his brain function is age appropriate. The patient is subjected to a SPECT brain perfusion scan.

As in Example 2, the resulting resized, spatially filtered and log transformed data is cross-correlated with a normal aging marker having a predetermined value for each pixel.

The resulting covariance value is compared to the distribution of values obtained in a normal population at the same chronological age. The clinician will use the invention to determine whether the subject's computed neurological age is within the normal limits established for individuals of comparable chronological age and demographics. Alternatively, if the chronologic age of a patient is not known, the clinician will use the subject's computed neurological age as an estimate of the true chronological age.

It is understood that the embodiments described hereinabove are merely illustrative and are not intended to limit the scope of the invention. It is realized that various changes, alterations, rearrangements and modifications can be made by those skilled in the art without substantially departing from the spirit and scope of the present invention.

| .1 | .1 | .1 | .1 | .1 | .1 | .1 | .1 | .1 | .1 | .1 | .1 | .1 | .1 | .1 | .1 |
|---|---|---|---|---|---|---|---|---|---|---|---|---|---|---|---|
| .1 | .1 | .1 | .1 | .1 | .1 | .1 | .1 | .1 | .1 | .1 | .1 | .1 | .1 | .1 | .1 |
| .1 | .1 | .1 | .1 | .1 | .1 | .1 | .1 | .1 | .1 | .1 | .1 | .1 | .1 | .1 | .1 |
| .1 | .1 | .1 | .1 | .1 | .1 | .1 | .1 | .1 | .1 | .1 | .1 | .1 | .1 | .1 | .1 |
| .1 | .1 | .1 | .1 | .1 | .1 | .1 | .1 | .1 | .1 | .1 | .1 | .1 | .1 | .1 | .1 |
| .1 | .1 | .1 | .1 | .1 | .1 | .1 | 1 | 1 | 2 | 2 | 3 | 3 | 3 | 2 | 1 |
| .1 | .1 | .1 | .1 | .1 | .1 | .1 | 1 | 1 | 2 | 3 | 3 | 4 | 4 | 4 | .1 |
| .1 | .1 | .1 | .1 | .1 | .1 | .1 | .1 | 1 | 2 | 3 | 4 | 5 | 5 | 5 | .1 |
| .1 | .1 | .1 | .1 | .1 | .1 | .1 | .1 | 2 | 3 | 4 | 5 | 6 | 6 | 7 | .1 |
| .1 | .1 | .1 | .1 | .1 | .1 | .1 | 2 | 3 | 4 | 5 | 6 | 7 | 8 | .1 |
| .1 | .1 | .1 | .1 | .1 | .1 | 1 | .1 | 2 | 3 | 4 | 5 | 6 | 6 | 7 | .1 |
| 1 | .1 | .1 | .1 | .1 | .1 | .1 | 1 | 2 | 3 | 4 | 5 | 5 | 5 | .1 |
| .1 | .1 | .1 | .1 | .1 | 1 | .1 | .1 | 1 | 2 | 3 | 3 | 4 | 4 | 4 | .1 |
| .1 | .1 | .1 | .1 | .1 | .1 | 1 | .1 | .1 | 1 | 2 | 2 | 3 | 3 | 3 | .1 |
| .1 | .1 | .1 | .1 | .1 | .1 | .1 | .1 | .1 | .1 | .1 | .1 | .1 | .1 | .1 | .1 |
| .1 | .1 | .1 | .1 | .1 | .1 | .1 | .1 | .1 | .1 | .1 | .1 | .1 | .1 | .1 | .1 |
| .1 | .1 | .1 | .1 | .1 | .1 | .1 | .1 | .1 | .1 | .1 | .1 | .1 | .1 | .1 | .1 |

-continued

| | | | | | | | | | | | | | | | |
|---|---|---|---|---|---|---|---|---|---|---|---|---|---|---|---|
| .1 | .1 | .1 | .1 | .1 | .1 | .1 | .1 | .1 | .1 | .1 | .1 | .1 | .1 | .1 | .1 |
| .1 | .1 | .1 | .1 | .1 | .1 | .1 | .1 | .1 | .1 | .1 | .1 | .1 | .1 | .1 | .1 |
| .1 | .1 | .1 | .1 | .1 | .1 | .1 | .1 | .1 | .1 | .1 | .1 | .1 | .1 | .1 | .1 |
| .1 | .1 | .1 | .1 | .1 | .1 | .1 | .1 | .1 | .1 | .1 | .1 | .1 | .1 | .1 | .1 |
| .1 | .1 | .1 | .1 | .1 | .1 | .1 | .1 | .1 | .1 | .1 | .1 | .1 | .1 | .1 | .1 |
| .1 | .1 | .1 | .1 | .1 | .1 | .1 | .1 | .1 | .1 | .1 | .1 | .1 | .1 | .1 | .1 |
| .1 | .1 | .1 | .1 | .1 | .1 | .1 | .1 | .1 | .1 | .1 | .1 | .1 | .1 | .1 | .1 |
| 4 | 4 | 4 | 4 | 3 | 3 | 3 | 2 | 2 | 1 | 1 | .1 | .1 | .1 | 1 | .1 |
| 5 | 5 | 5 | 5 | 4 | 4 | 4 | 3 | 3 | 2 | 1 | .1 | .1 | .1 | 1 | .1 |
| 6 | 6 | 6 | 6 | 5 | 5 | 5 | 4 | 3 | 2 | 1 | .1 | .1 | .1 | .1 | .1 |
| 7 | 8 | 6 | 7 | 7 | 6 | 6 | 5 | 4 | 3 | 2 | 1 | .1 | 1 | .1 | .1 |
| 9 | 10 | 10 | 9 | 8 | 7 | 6 | 5 | 4 | 3 | 2 | 1 | .1 | 1 | .1 | .1 |
| 7 | 5 | 8 | 7 | 7 | 6 | 6 | 5 | 4 | 3 | 2 | 1 | .1 | 1 | .1 | .1 |
| 6 | 6 | 6 | 6 | 5 | 5 | 5 | 4 | 3 | 2 | 1 | 1 | .1 | .1 | 1 | .1 |
| 5 | 5 | 5 | 5 | 4 | 4 | 4 | 3 | 3 | 2 | 1 | .1 | 1 | .1 | 1 | .1 |
| 4 | 4 | 4 | 4 | 3 | 3 | 3 | 2 | 2 | 1 | 1 | .1 | .1 | .1 | .1 | .1 |
| .1 | .1 | .1 | .1 | .1 | .1 | .1 | .1 | .1 | .1 | .1 | .1 | .1 | .1 | .1 | .1 |
| .1 | .1 | .1 | .1 | .1 | .1 | .1 | .1 | .1 | .1 | .1 | .1 | .1 | .1 | .1 | .1 |
| .1 | .1 | .1 | .1 | .1 | .1 | .1 | .1 | .1 | .1 | .1 | .1 | .1 | .1 | .1 | .1 |
| .1 | .1 | .1 | .1 | .1 | .1 | .1 | .1 | .1 | .1 | .1 | .1 | .1 | .1 | .1 | .1 |
| .1 | .1 | .1 | .1 | .1 | .1 | .1 | .1 | .1 | .1 | .1 | .1 | .1 | .1 | .1 | .1 |

TABLE II

TABLE III

| | | | | | | | |
|---|---|---|---|---|---|---|---|
| .1 | .1 | .1 | .1 | .1 | .1 | .1 | .1 |
| .1 | .1 | .1 | .558 | .875 | .25 | .1 | .1 |
| .1 | .1 | 1.358 | 3.25 | 3.75 | 2.5 | .408 | .1 |
| .1 | .25 | 3.167 | 6.417 | 7.5 | 5 | 1.283 | .1 |
| .1 | .175 | 2.833 | 5.333 | 5.5 | 4.333 | 1.042 | .1 |
| .1 | .1 | .642 | 2.25 | 2.75 | 1.517 | .175 | .1 |
| .1 | .1 | .1 | .175 | .325 | .1 | .1 | .1 |
| .1 | .1 | .1 | .1 | .1 | .1 | .1 | .1 |

TABLE IV

| | | | | | | | |
|---|---|---|---|---|---|---|---|
| −2.3026 | −2.3026 | −2.3026 | −2.3026 | −2.3026 | −2.3026 | −2.3026 | −2.3026 |
| −2.3026 | −2.3026 | −2.3026 | −0.5834 | −0.1335 | −1.3863 | −2.3026 | −2.3026 |
| −2.3026 | −2.3026 | 0.30601 | 1.17866 | 1.32176 | 0.91629 | −0.8965 | −2.3026 |
| −2.3026 | −1.3863 | 1.15278 | 1.85895 | 2.0149 | 1.60944 | 0.2492 | −2.3026 |
| −2.3026 | −1.743 | 1.04134 | 1.67391 | 1.70475 | 1.46626 | 0.04114 | −2.3026 |
| −2.3026 | −2.3026 | −0.4432 | 0.81093 | 1.0116 | 0.41673 | −1.743 | −2.3026 |
| −2.3026 | −2.3026 | −2.3026 | −1.743 | −1.1239 | −2.3026 | −2.3026 | −2.3026 |
| −2.3026 | −2.3026 | −2.3026 | −2.3026 | −2.3026 | −2.3026 | −2.3026 | −2.3026 |

TABLE V
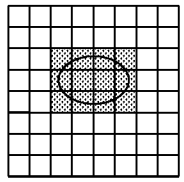
TABLE VI
| Z (mm) | Xe (mm) | Ye (mm) | R1 (mm) | R2 (mm) | Ang (deg.) | $P_{VOI}$ LH | RH |
|---|---|---|---|---|---|---|---|
| −28 | −31 | −64 | 21 | 27 | −57 | 1.52 | 1.66 |
| −24 | −30 | −69 | 19 | 24 | −59 | 1.52 | 1.66 |
| −24 | −1 | −25 | 14 | 16 | 87 | 2.11 | 2.11 |
| −20 | −29 | −67 | 17 | 24 | −66 | 1.52 | 1.66 |
| −20 | −2 | −24 | 14 | 15 | −89 | 2.11 | 2.11 |
| −16 | −48 | −14 | 33 | 10 | −87 | −1.47 | −0.58 |
| −12 | −50 | −12 | 28 | 10 | −86 | −1.47 | −0.58 |
| −12 | −1 | −21 | 16 | 14 | −86 | −.042 | −0.42 |
| −8 | −50 | −13 | 27 | 11 | −86 | −1.47 | −0.58 |
| −8 | 0 | −22 | 16 | 12 | −86 | −0.42 | −0.42 |
| −1 | −24 | −2 | 20 | 8 | −78 | 1.22 | 1.49 |
| −1 | −9 | 14 | 9 | 6 | 61 | 0.46 | 0.84 |
| −1 | −45 | 33 | 16 | 9 | −89 | −0.55 | −0.48 |
| −1 | −10 | 47 | 20 | 7 | −89 | −0.74 | −0.65 |
| 4 | −23 | −3 | 19 | 8 | −74 | 1.22 | 1.49 |
| 4 | −9 | 13 | 11 | 6 | 69 | 0.46 | 0.84 |
| 4 | −45 | 31 | 15 | 10 | −86 | −0.55 | −0.48 |
| 4 | −11 | 49 | 19 | 9 | −86 | −0.74 | −0.65 |
| 4 | −10 | −20 | 16 | 7 | −62 | 1.04 | 0.78 |
| 4 | −12 | −77 | 25 | 9 | 88 | −0.29 | −0.42 |
| 4 | −46 | −57 | 37 | 11 | 70 | −0.18 | 0.49 |
| 8 | −25 | −3 | 6 | 19 | 12 | 1.22 | 1.49 |
| 8 | −11 | 14 | 6 | 11 | −32 | 0.46 | 0.84 |
| 8 | −12 | −17 | 8 | 15 | 22 | 1.04 | 0.78 |
| 8 | −44 | 36 | 10 | 16 | 21 | −0.55 | −0.48 |
| 8 | −12 | 50 | 9 | 18 | −2 | −0.74 | −0.65 |
| 8 | −12 | −73 | 26 | −2 | −0.29 | −0.42 | |
| 8 | −46 | −61 | 12 | 33 | −25 | −0.18 | 0.49 |
| 12 | −25 | −4 | 6 | 15 | 14 | 1.22 | 1.49 |
| 12 | −12 | 11 | 5 | 9 | −19 | 0.46 | 0.84 |
| 12 | −12 | −18 | 7 | 14 | 23 | 1.04 | 0.78 |
| 12 | −43 | 28 | 11 | 18 | 7 | −0.55 | −0.48 |
| 12 | −12 | 48 | 8 | 18 | 0 | −0.74 | −0.65 |
| 12 | −11 | −71 | 9 | 24 | 0 | −0.29 | −0.42 |
| 12 | −46 | −58 | 11 | 30 | −26 | −0.18 | 0.49 |
| 16 | −12 | 45 | 8 | 20 | 2 | −0.74 | −0.65 |
| 20 | −12 | 41 | 8 | 22 | 0 | −0.74 | −0.65 |
| 24 | −46 | 16 | 12 | 28 | 13 | −1.2 | −0.86 |
| 24 | −49 | −49 | 12 | 21 | −9 | −0.95 | 0.03 |
| 24 | −14 | −76 | 11 | 17 | −1 | −1.31 | −0.97 |
| 28 | −46 | 13 | 12 | 24 | 12 | −1.2 | −0.86 |
| 28 | −45 | −54 | 12 | 24 | −27 | −0.95 | 0.03 |
| 28 | −12 | −74 | 11 | 17 | −2 | 1 | −0.97 |
| 32 | −41 | 15 | 13 | 23 | 13 | −1.2 | −0.86 |
| 32 | −47 | −43 | 12 | 20 | −6 | −0.95 | 0.03 |
| 32 | −12 | −73 | 11 | 15 | 3 | −1.31 | −0.97 |
| 35 | −42 | 14 | 12 | 25 | 17 | −1.2 | −0.86 |
| 35 | −47 | −47 | 11 | 19 | −9 | −0.95 | 0.03 |
| 40 | −11 | 18 | 11 | 33 | 1 | −1.55 | −0.79 |
| 45 | −11 | 7 | 9 | 38 | 1 | −1.55 | −0.79 |
TABLE VII
| | | | | | | | | | | | | | | | |
|---|---|---|---|---|---|---|---|---|---|---|---|---|---|---|---|
| −.01 | −.01 | −.01 | −.01 | −.01 | −.01 | −.01 | −.01 | −.01 | −.01 | 2.11 | 2.11 | 2.11 | 2.11 | −.01 | −01 |
| −.01 | −.01 | −.01 | −.01 | −.01 | −.01 | −.01 | −.01 | −.01 | −.01 | 2.11 | 2.11 | 2.11 | 2.11 | −.01 | −.01 |

TABLE VII-continued

| | | | | | | | |
|---|---|---|---|---|---|---|---|
| −.01 | −.01 | 2.11 | 2.11 | 2.11 | 2.11 | −01 | −.01 |
| −.01 | −.01 | −.01 | −.01 | −.01 | −.01 | −.01 | −.01 |
| −.01 | −.01 | −.01 | −.01 | −.01 | −.01 | −.01 | −.01 |
| −.01 | −.01 | −.01 | −.01 | −.01 | −.01 | −.01 | −.01 |

TABLE VIII

| | | | | | | | |
|---|---|---|---|---|---|---|---|
| 0.02303 | 0.02303 | 0.02303 | 0.02303 | 0.02303 | 0.02303 | 0.02303 | 0.02303 |
| 0.02303 | 0.02303 | 0.02303 | 0.00583 | 0.00134 | 0.01386 | 0.02303 | 0.02303 |
| 0.02303 | 0.02303 | 0.64569 | 2.48696 | 2.7889 | 1.93337 | 0.00896 | 0.02303 |
| 0.02303 | 0.01386 | 2.43238 | 3.92239 | 4.25145 | 3.39591 | −0.0025 | 0.02303 |
| 0.02303 | 0.01743 | 2.19722 | 3.53196 | 3.59702 | 3.09381 | 0.0004 | 0.02303 |
| 0.02303 | 0.02303 | 0.00443 | −0.0081 | −0.0101 | −0.0042 | 0.01743 | 0.02303 |
| 0.02303 | 0.02303 | 0.02303 | 0.01743 | 0.01124 | 0.02303 | 0.02303 | 0.02303 |
| 0.02303 | 0.02303 | 0.02303 | 0.02303 | 0.02303 | 0.02303 | 0.02303 | 0.02303 |

What is claimed is:

1. A method for producing a marker for use in screening patients for nervous system dysfunction, comprising:
   predetermining a plurality of sets of coordinates of a given brain geometry; and
   predetermining functional activity at each of said plurality of sets of predetermined coordinates of said given brain geometry to produce a marker for use in screening patients for nervous system dysfunction.

2. The according to claim 1, wherein each set of predetermined coordinates has a single numerical value associated corresponding to functional activity.

3. The method according to claim 1, wherein each set of coordinates corresponds to a volume of interest in a patient's brain.

4. The method according to claim 3, wherein each volume of interest is no greater than about 1 cm$^3$.

5. The method according to claim 3, wherein each volume of interest corresponds to at least one pixel of at least one slice of a corresponding brain scan.

6. The method according to claim 5, wherein the profile comprises an array of values, said value being associated with at least one said pixel for each slice of the corresponding brain scan.

7. The method according to claim 1, wherein said functional activity is profiled in a population of patients having Parkinson's disease.

8. The method according to claim 1, wherein said functional activity is profiled in a population of patients having Huntington's disease.

9. The method according to claim 1, wherein said functional activity is profiled in a population of patients having Alzheimer's disease.

10. The method according to claim 1, wherein said functional activity is profiled in a population of patients having depression.

11. A method of creating a marker for use in screening patients for a particular nervous system dysfunction, comprising: selecting a nervous system dysfunction; and creating a three-dimensional numeric array of volume values for a brain having said particular nervous system dysfunction, said array representing the marker.

12. The method according to claim 11, wherein each said volume value has a single numerical value associated therewith corresponding to functional activity.

13. The method according to claim 11, wherein each said volume value corresponds to a region of interest in a patient's brain.

14. The method according to claim 13, wherein each said volume value is no greater than about 1 cm$^3$.

15. The method according to claim 13, wherein each said volume value corresponds to at least one pixel of at least one slice of a corresponding brain scan.

16. The method according to claim 15, wherein the three-dimensional array comprises a two-dimensional array of values for each slice of the corresponding brain scan.

17. The method according to claim 11, wherein the selected nervous system dysfunction is Parkinson's disease.

18. The method according to claim 11, wherein the selected nervous system dysfunction is Huntington's disease.

19. The method according to claim 11, wherein the selected nervous system dysfunction is Alzheimer's disease.

20. The method according to claim 11, wherein the selected nervous system dysfunction is depression.

21. Apparatus for screening for nervous system dysfunction in a patient, comprising
   a marker produced by the method of claim 1, 2, 3, 4, 5, 6, 7, 8, 9, 10, 11, 12, 13, 14, 15, 16, 17, 18, 19 or 20;
   a cross-correlator operative upon said marker and a patient profile for producing a cross-correlated patient profile; and
   a post processor operative on said cross-correlated patient profile to screen for nervous system dysfunction in the patient.

* * * * *

UNITED STATES PATENT AND TRADEMARK OFFICE
CERTIFICATE OF CORRECTION

PATENT NO. : 5,873,823
DATED : February 23, 1999
INVENTOR(S) : Eidelberg, et al.

It is certified that error appears in the above-identified patent and that said Letters Patent is hereby corrected as shown below:

In Claim 2, column 15, line 31, insert the word --method-- immediately preceding 'according'.

In Claim 6, column 15, line 43, insert the word --each-- immediately preceding 'said'.

Signed and Sealed this

Sixth Day of July, 1999

Attest:

Q. TODD DICKINSON

*Attesting Officer*  Acting Commissioner of Patents and Trademarks